United States Patent [19]

Fitzig et al.

[11] Patent Number: 4,701,128
[45] Date of Patent: Oct. 20, 1987

[54] HANDHELD GRINDING DEVICE FOR CROWN PREPARATION

[76] Inventors: Simon Fitzig, 68 Ibn Gvirol Street; Ervin Weiss, 18 Kley Street, both of Tel-Aviv, Israel

[21] Appl. No.: 810,583

[22] Filed: Dec. 19, 1985

[30] Foreign Application Priority Data

Jan. 4, 1985 [IL] Israel ............ 74003

[51] Int. Cl.⁴ .............................. A61C 1/16
[52] U.S. Cl. .................... 433/116; 433/142
[58] Field of Search ............. 433/142, 166, 116

[56] References Cited

U.S. PATENT DOCUMENTS

| | | | |
|---|---|---|---|
| 319,237 | 6/1885 | Grout | 433/116 |
| 635,244 | 10/1899 | Gholson | 433/116 |
| 1,093,865 | 4/1914 | Lauderdale | 433/116 |
| 2,176,339 | 10/1939 | Henneman | 433/116 |
| 2,287,260 | 6/1942 | Luck | 433/116 |
| 2,429,356 | 10/1947 | Hicks | 433/116 |
| 3,786,566 | 1/1974 | Jelicic et al. | 433/116 |

*Primary Examiner*—John J. Wilson
*Assistant Examiner*—Adriene J. Lepiane
*Attorney, Agent, or Firm*—Benjamin J. Barish

[57] ABSTRACT

A handheld dental tool for crown preparation, comprises a handle, a grinding burr, and a guard attached to the handle. The guard has a tip solid spherical closely spaced from the tip of the grinding burr such as to be receivable between the tooth to be prepared and the free gingival tissue thereat to protect the gingival tissue during the grinding of the tooth.

11 Claims, 3 Drawing Figures

HANDHELD GRINDING DEVICE FOR CROWN PREPARATION

BACKGROUND OF THE INVENTION

The present invention relates to a handheld grinding device. The invention is particularly useful as a dental tool for crown preparation, and is therefore described below with respect to this application, although it will be appreciated that the invention could also advantageously be used in other applications.

Preparation of a crown usually requires grinding the tooth enamel to the sub-gingival margin, particularly in the preparation of frontal upper teeth for porcelain crowns. Grinding the tooth at the sub-gingival margin, however, frequently causes damage to the adjacent gingival tissue. Such damage not only results in considerable patient discomfort, but can also cause irreversible gingival retraction and local edema. The latter, when it occurs, often forces the dentist to postpone continuation of the treatment, e.g. of taking impressions for working models, until the area heals.

A small percentage of dentists use guards for protecting the gingival during grinding of the tooth for crown preparation. However, such guards are difficult to set in place, and often become dislodged. Moreover, using them is very time-consuming, particularly since they must be reset each time the dentist wishes to prepare another tooth. Further, the known guards provide, at best, very limited protection. These drawbacks stem, in large part, from the static nature of the guard; and because of these problems, most dentists do not use any protection whatsoever.

SUMMARY OF THE INVENTION

An object of the present invention is to provide a handheld grinding device particularly useful as a dental tool for crown preparation and having advantages in the above respects.

According to the present invention, there is provided a handheld grinding device particularly useful as a dental tool for crown preparation including a handle and a grinding burr rotatable about a rotary axis, in which the grinding device further includes a guard having a stem attached to the handle. The stem includes an inner mounting section and an outer section of solid cylindrical configuration extending laterally of and generally parallel to the rotary axis of the grinding burr. The outer section of the stem terminates in a solid spherical tip closely spaced from the tip of the grinding burr such as to be receivable between the tooth to be prepared and the free gingival tissue thereat to protect the gingival tissue during the grinding of the tooth.

In the preferred embodiment of the invention described below, the rotary axis of the burr is generally perpendicular to the axis of the handle, and the stem inner section of the stem is generally parallel to the axis of the handle and is joined to the outer section by a curved juncture.

It will thus by seen that the device of the present invention is a dynamic device, as distinguished from a static device heretofore used, and therefore is not subject to the same drawbacks of requiring setting up and resetting each time another tooth is to be prepared. Thus, the invention provides a high level of efficiency in eliminating gingival damage, wastes no time in patient preparation, enables all sides of the tooth to be prepared without causing damage, and allows taking impressions at the same session.

According to further features included in the described preferred embodiment, the stem is carried by a collar attached to the handle, and the collar includes a socket, and has means for selectively attaching therein guards of different sizes and/or configurations, and means permitting varying the distance of the solid spherical tip from the burr according to the particular condition of the patient's teeth then been worked on.

The invention also provides an attachment to a grinding device, particularly useful as a dental tool for crown preparation.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

Figure 1:
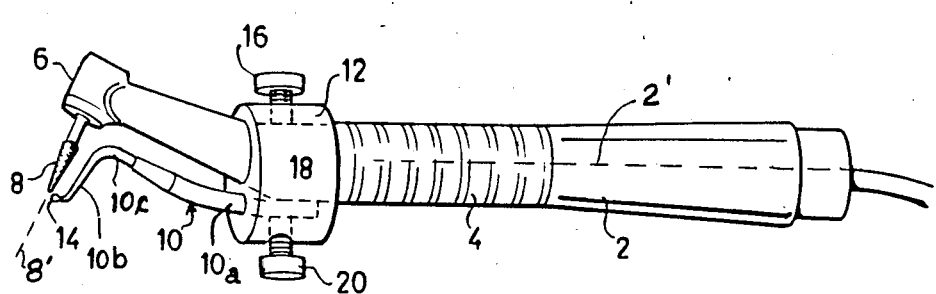
FIG. 1 is a side elevational view illustrating one form of handheld grinding device constructed in accordance with the present invention particularly useful as a dental tool for crown preparation.

The handheld grinding device illustrated in FIG. 1 is particularly useful as a dental tool for crown preparation. It comprises a handle 2 formed with a plurality of knurled rings 4 to facilitate gripping by the dentist. The opposite end of the device includes a head 6 receiving a grinding burr having a rotary axis 8' generally perpendicular to the axis 2' of the handle, 8 for grinding the enamel of the tooth when preparing a crown. Such grinding devices, insofar as described above, are well known and commonly available, and therefore further details of its construction or operation are not deemed necessary.

The device illustrated in FIG. 1 further includes a guard 10 attached at one end to the handle by means of a collar 12, the opposite end of the guard terminating in a solid spherical tip 14 so as to be closely spaced to the tip of the grinding burr 8. Collar 12 may be attached to handle 4 by a fastener 16. Collar 12 includes a socket 18 for receiving guard 10, the stem being fixed to collar 12 by another fastener 20.

Guard 10 is in the form of a stem having a rigid inner mounting section 10a at one end generally parallel to the axis 2' of the handle 2, an outer section 10b of cylindrical configuration extending laterally of and generally parallel to the rotary axis 8' of the burr 8, and a curved juncture 10c between these two sections. The solid spherical tip 14 is preferrably highly polished, and should be located a small fraction of a millimeter, e.g. 0.01 to 0.06 mm, from the tip of burr 8. As shown in FIG. 1, the mounting section 10a of the stem 10 is preferably of relatively large diameter, the diameter decreasing towards the solid spherical tip 14. Preferably, stem 10 is made of stainless steel.

Fastener 20 is in the form of a threaded pin engageable with the mounting section 10a of the stem and received within the socket 18. Thus, threaded pin 20 selectively permits guards of different sizes and/or configurations to be attached to socket 18, and also permits varying the mounting position of the guard stem 10, and thereby the spacing of the solid spherical tip 14 from the tip of the burr 8, according to the particular conditions of the patient's teeth then being worked on.

Figure 2:
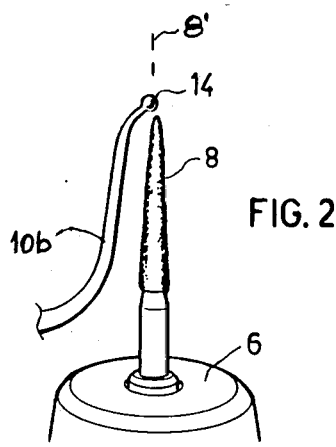
FIG. 2 is an enlarged view better showing the tip of the guard attachment with respect to the grinding burr.
Figure 3:
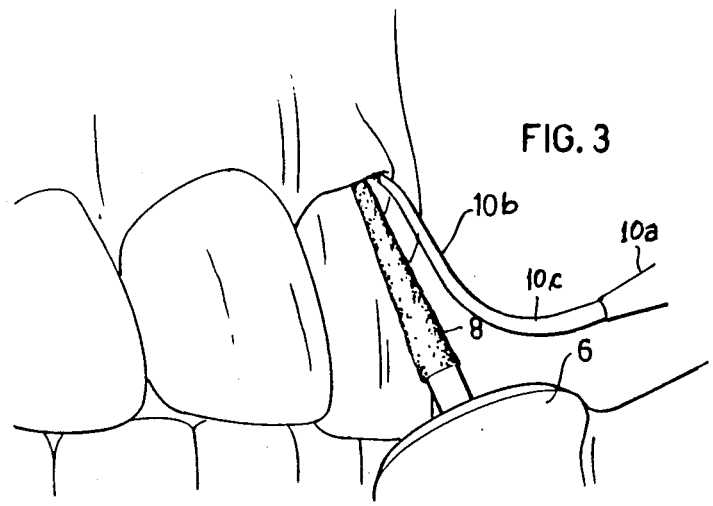
FIG. 3 illustrates the manner of using the grinding device of FIGS. 1 and 2 for crown preparation.

FIG. 3 illustrates the manner of using the device of FIGS. 1 and 2 for protecting the gingival tissue while using burr 8 for grinding the tooth enamel in order to prepare a crown. During this operation, the solid spherical tip 14 of the guard 10 is inserted into the free gingival prior to grinding, so that tip 14 causes retraction of the gingival and prevents the end of the burr from coming into contact with the unattached gingival.

While the invention has been described with respect to one preferred embodiment, it will be appreciated that many variations may be made. Thus, instead of having the collar selectively receive guards of different sizes and/or configurations, it will be appreciated that a collar could be provided for each individual guard. It will also be appreciated that the guard could be secured to the handle in another manner, for example by the use of a bonding agent for bonding it to the handle. Further, besides use as a dental tool for crown preparation, the guard could also be used as a grinding or burnishing tool for various other purposes, particularly medical purposes, in which grinding is carried out adjacent to tissue which may be injured by the grinding operation.

Many other variations, modifications and applications of the invention will be apparent.

What is claimed is:

1. A handheld grinding device particularly useful as a dental tool for crown preparation including a handle and a grinding burr rotatable about a rotary axis, characterized in that said device further includes a guard having a stem attachable to said handle, said stem including an inner mounting section and an outer section of a solid cylindrical configuration extending laterally of and generally parallel to the rotary axis of the grinding burr, said outer section of the stem terminating in a solid spherical tip closely spaced from the tip of the grinding burr such as to be receivable between a tooth to be prepared and the free gingival tissue thereat to protect the gingival tissue during the grinding of the tooth.

2. The device according to claim 1, wherein said rotary axis of the grinding burr is generally perpendicular to the axis of said handle, said inner mounting section of the stem being generally parallel to the axis of the handle, and being joined to the outer stem section by a curved juncture.

3. The device according to claim 1, wherein said solid spherical tip of the stem is spaced within a small fraction of a millimeter from the tip of the burr.

4. The device according to claim 1, wherein said stem is carried by a collar attached to said handle.

5. The device according to claim 4, wherein said collar includes a socket, and means for selectively attaching therein guards of different sizes and/or configurations.

6. The device according to claim 4, wherein said collar includes a threaded pin engageable with the stem when received within said socket permitting varying the distance of said solid spherical tip from the burr.

7. An attachment to a grinding device particularly useful as a dental tool for crown preparation having a grinding burr rotatable about a rotary axis, comprising:
a collar attachable to the handle of the grinding device, and a guard carried by said collar and having a stem including an inner mounting section attached to the collar and outer section of a solid cylindrical configuration extending generally laterally of and parallel to the rotary axis of the burr, said outer section of the stem terminating in a solid spherical tip closely spaced from the tip of the grinding burr such as to be receivable between a tooth to be prepared and the free gingival tissue thereat to protect the gingival tissue during the grinding of the tooth.

8. The attachment according to claim 7, wherein said rotary axis of the burr is generally perpendicular to the axis of the said handle, said inner mounting section of the stem being generally parallel to the axis of the handle and being joined to the outer section by a curved juncture.

9. The attachment according to claim 7, wherein said solid spherical tip of the stem is spaced within a small fraction of a millimeter from the tip of the grinding burr.

10. The attachment according to claim 7, wherein said collar includes a socket, and means for selectively attaching therein guards of different sizes and/or configurations.

11. The attachment according to claim 7, wherein said collar includes a threaded pin engageable with the inner mounting section of the stem when received within said socket and permitting varying the spacing of said solid spherical tip from the grinding burr.

* * * * *